United States Patent [19]

Costa et al.

[11] Patent Number: 5,189,026

[45] Date of Patent: Feb. 23, 1993

[54] TREATMENT OF HUMAN DISEASES INVOLVING DYSREGULATION OR DYSFUNCTION OF THE NERVOUS SYSTEM

[75] Inventors: Jonathan L. Costa, Wheaton, Ill.; Jesus A. Diazgranados, Cali, Colombia

[73] Assignee: Fractal Laboratories, Inc., Newton, N.J.

[21] Appl. No.: 711,759

[22] Filed: Jun. 7, 1991

[51] Int. Cl.$^5$ ............................................. A61K 31/70
[52] U.S. Cl. ..................................... 514/30; 514/903; 514/906
[58] Field of Search .......................... 514/30, 903, 906

[56] References Cited

U.S. PATENT DOCUMENTS

| | | | |
|---|---|---|---|
| 4,171,314 | 10/1979 | Chabala et al. | 260/343.41 |
| 4,173,571 | 11/1979 | Chabala et al. | 260/343.41 |
| 4,199,569 | 4/1980 | Chabala et al. | 424/180 |
| 4,201,861 | 5/1980 | Mrozik et al. | 536/17 A |
| 4,206,205 | 6/1980 | Mrozik et al. | 424/180 |
| 4,310,519 | 1/1982 | Albers-Schonberg et al. | 424/181 |
| 4,333,925 | 6/1982 | Buhs et al. | 424/181 |
| 4,831,017 | 5/1989 | Egerton | 514/30 |
| 4,853,372 | 8/1989 | Williams et al. | 514/30 |
| 4,963,667 | 10/1990 | Chiu et al. | 536/7.1 |
| 5,070,015 | 12/1991 | Pentuch et al. | 514/30 |

OTHER PUBLICATIONS

Avery's Drug Treatment, 3rd edition, AIDS Press (1987) pp. 1114–1116.
Bennett, Javma, 189, 100–104, (1986).
Chalmers, et al., Em. J. Pharmacol., 129, 371–374, (1986).
Martin, et al., Br. J. Pharmacol., 98, 747–756, (1989).
Mart, Resland News, 151, 1317, (1991).
Gisslinger, et al., Lancet, 336, 1078 (1990).
Levine, et al., Science, 226, 547–49 (1984).
Thompson, et al., Ann. Rheum. Dis. 21, 370–77 (1962).
Bland, et al., Arthritis and Rheum., 11, 72–79, (1968).
Kugelber, Electroceneph. Clin. Neurophysiol. Suppl 22 103–111 (1962).
Pacque, et al., Lancet, 335, 1377–1380 (1990).
Pacque, et al., Lancet, 336, 1486–89 (1990).
Campbell, et al., Science, 221, 823–828, (1983).
Campbell, et al., J. Vet. Pharmacol. Therap., 7 1–16, (1984).
Terada, et al., Exp. Parasitol., 57 149–157 (1984).
Hagbarth, J. Neurol. Neurosurg. Psychia., 23 222–227 (1960).
Hagbarth, et al., J. Neurol. Neurosurg. Psychia., 31 207–213 (1968).
Hassan et al., J. Neurol Neurosurg. Pschia., 43 1132–1136 (1980).
Knutsson, Triangle, 21, 13–20 (1982).
Knutsson, et al., Scand. J. Rehabil. Med., 12, 93–106 (1980).
Knutsson, et al., J. Neurol. Sci., 53, 187–204 (1982).
McNamara, et al., Neuropharmacol., 27, 563–68 (1988).
McNamara, Epilepsia, 30, 513–518 (1989) (Suppl. 1).
Coward, Triangle, 20, 151–158 (1981).
Davies, Br. J. Pharmacol., 76, 473–481 (1982).
Davies, et al., Br. J. Pharmacol., 78, 137–142 (1983).
Sayers, et al., Arzneimitted-Forschung, 30, 793–803 (1980).
Kerr, et al., Brain Res., 405, 150–154 (1987).
Price, et al., Nature, 307 71–74 (1984).
Bowery et al., Neuropharmacol., 23, 219–234 (1984).
Olsen, et al., Fase, B. J., 4, 1469–1480 (1990).
Erickson, Sci. Amer., 264 (5) 124 (1991).
Porter, et al., Cleveland Clin. Quart., 51, 293–305 (Summer 1984).
Sigel, et al., Mol. Pharmacol., 32, 749–52 (1987).
Soderlund, et al., Biochem. Biophys. Res. Comm. 146, 692–698 (1987).
Kirkness, et al., Eur. J. Pharmacol., 150, 385–388 (1983).
Robertson, Br. J. Pharmacol., 98, 167–176 (1989).
Chu, et al., Neurol., 37, 1454–59 (1987).
Bhisitkul, et al., Exp. Brain Res., 66, 659–663 (1987).
Crichlow et al., Neuropharmacology, 25 (10, 1085–1088 (1986).
Diggs et al., Laboratory Animal Science, 40 (1), 68–71 (1990).

Primary Examiner—Frederick E. Waddell
Assistant Examiner—Raymond J. Henley, III
Attorney, Agent, or Firm—Gerald S. Rosen

[57] ABSTRACT

A method of preventing, treating and/or controlling diseases caused by dysregulation and/or dysfunction of various portions of the nervous system which comprises administering to a patient, an effective amount of a compound of the avermectin family, e.g. ivermectin, in single or multiple doses of up to 1.6 mg/kg at intervals of from 3 days to 4 months.

9 Claims, No Drawings

TREATMENT OF HUMAN DISEASES INVOLVING DYSREGULATION OR DYSFUNCTION OF THE NERVOUS SYSTEM

BACKGROUND

1. Field of Invention

This invention relates to the use of the C-076 family of compounds, i.e. avermectins, for the prevention, treatment and control of various diseases in humans caused by dysregulation and/or dysfunction of various portions of the human nervous system. More particularly, this invention relates to the administration of the avermectin class of compounds (1) to prevent, treat, and control such diseases in humans as seizures, dystonic movements, tremors, degenerative conditions of the brain, spinal cord, and peripheral nerves, spasticity of both brain and spinal cord origin, and various types of psychoses and personality disorders, (2) to increase tonic activity of the parasympathetic nervous system, as in bladder and bowel control, (3) to decrease activity of the sympathetic nervous system at cutaneous and cardiovascular levels, (4) to ameliorate depression, (5) to regularize the sleep-wake cycle, (6) to decrease addictive and abusive behavior, (7) to increase attention span and improve behavior of mentally-deficient children and adults, (8) to treat autoimmune disorders, (9) to treat malignant states, and (10) to prevent or ameliorate anoxic or ischemic damage to the nervous system, as well as specific pharmaceutical formulations and treatment regimens for such prevention, treatment and control. The preferred compound which is used to illustrate this invention is ivermectin. Ivermectin is a semi-synthetic derivative of avermectin and is generally produced as a mixture of at least 80% 22,23-dihydroavermectin $B_{1a}$ and less than 20% 22,23-dihydroavermectin $B_{1b}$. The following structural formula represents the avermectin series of compounds, which compounds can be chemically converted to useful derivatives as discussed below.

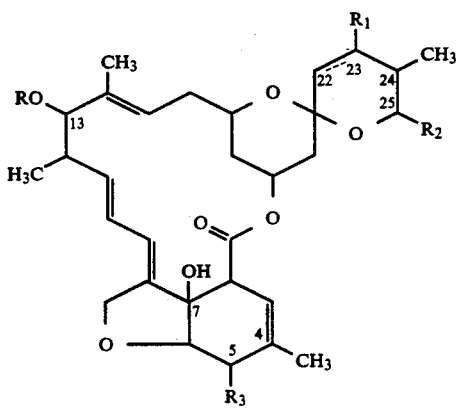

wherein R is the 4'-(alpha-L-oleandrosyl)-alpha-L-oleandrose group of the structure:

and wherein the broken line indicates a single or double bond; $R_1$ is hydroxy and is present only when said broken line indicates a double bond; $R_2$ is isopropyl or sec-butyl; and $R_3$ is methoxy or hydroxy.

2. Prior Art

The avermectin family, of which ivermectin, a chemically produced analog, is a member, is a series of compounds isolated from the fermentation broth of a C-076 producing strain of Streptomyces avermitillis and also chemically produced derivatives thereof. At least eight distinct but closely related compounds are produced by S. avermitillis, $A_{1a}$, $A_{1b}$, $A_{2a}$, $A_{2b}$, $B_{1a}$, $B_{1b}$, $B_{2a}$, and $B_{2b}$. Their production is described in U.S. Pat. No. 4,310,519. The preparation of ivermectin is disclosed in U.S. Pat. No. 4,199,569. The disclosures of each of the foregoing patents are incorporated herein by reference. The avermectin family of compounds is a series of very potent antiparasitic agents known to be useful against a broad spectrum of endoparasites and ectoparasites in mammals and also to have agricultural uses against various nematode and insect parasites found in and on crops and in soil.

Some of the avermectins contain a 22,23-double bond. This may be selectively reduced to prepare the ivermectin compounds. In addition, the avermectins possess a disaccharide moiety at the 13-position consisting of the alpha-L-oleandrosyl-alpha-L-oleandrosyl group. One or both of these saccharide groups may be removed as described in U.S. Pat. No. 4,206,205. The thus produced aglycone derivatives have a hydroxy group at the 13-position. This group may be removed to form the 13-deoxy compound as described in U.S. Pat. Nos. 4,171,314 and 4,173,571; the latter patent also describes the 13-halo derivatives. The avermectin compounds and derivatives have several hydroxy groups which may be acylated as described in U.S. Pat. No. 4,201,861. Other derivatives of avermectin and ivermectin are disclosed in U.S. Pat. Nos. 4,333,925 and 4,963,667. All the aforementioned patents are incorporated herein by reference. The compounds disclosed in the patents mentioned above share the property of antiparasitic activity with ivermectin.

Since all the compounds mentioned and referred to above share the spectrum of anti-parasitic biological activity of ivermectin, varying only in degree, it is expected they will share the activity spectrum needed to make them suitable for use in this invention. In order to establish their potency and selectivity as compared to invermectin, other members of the avermectin class could be screened utilizing in vitro and in vivo models already known from the literature. Compounds which look promising for preventing, treating or controlling a particular indication in the in vitro screens are tested further in animal models. Those with the potency desired in the animal models are then further selected for testing in human pharmacodynamic models and clinical trials.

In vitro screens which are suitable include (1) the binding of the test compounds as radio labeled derivatives thereof to preparations of gamma-aminobutyric acid (GABA) receptors, sub-types A and B, (2) the displacement of the binding of other known GABA A and B receptor agonists by the avermectin compounds, (3) examination of the ability of either the avermectin compounds, or of other GABA agonists plus the avermectin compounds, to bind in the presence of GABA, and (4) effects of the avermectin compounds on the release and uptake of GABA by brain or nerve preparations. The tests described herein are disclosed in the following publications: Sigel, et al. Mol. Pharmacol., 32, 749–52 (1987); Soderlund, et al., Biochem. Biophys. Res. Comm. 146, 692–698 (1987); Kirkness, et al., Eur. J. Pharmacol., 150, 385–388 (1988); Robertson, Br. J. Pharmacol., 98, 167–176 (1989); Chu, et al., Neurol., 37, 1454–1459 (1987); Bhisitkul, et al., Exp. Brain Res., 66, 659–663 (1987); Kerr, et al., Brain Res., 405, 150–154 (1987); Price, et al., Nature, 307, 71–74 (1984); Bowery, et al., Neuropharmacol., 23, 219–231 (1984); Olsen, et al., FASEB J., 4, 1469–1480 (1990); and Erickson, Sci. Amer., 264(5), 124 (1991). All four types of assays can be performed using GABA preparations derived from different regions of the brain, spinal cord, peripheral nerves, and various body organs.

In vivo screens suitable for testing include using animal models for seizures and for spasticity. Suitable seizure models are disclosed in Porter, et al., Cleveland Clin. Quart., 51, 293–305 (summer 1984); McNamara, et al., Neuropharmacol., 27, 563–568 (1988); and McNamara, Epilepsia, 30 suppl, 513–518 (1989). Suitable spasticity models are disclosed in Coward, Triangle, 20, 151–158 (1981); Davies, Br. J. Pharmacol., 76, 473–481 (1982); Davies, et al., Br. J. Pharmacol., 78, 137–142, (1983), and Sayers, et al., Arzneimittel-Forschung, 30, 793–803 (1980).

Comparative human pharmacodynamic studies are then conducted using the compounds with the particular biological profile predicted from the in vitro and animal screens. The human tests which are suitable are disclosed in Hagbarth, J. Neurol. Neurosurg. Psychia., 23, 222–227 (1960); Hagbarth, et al., J. Neurol. Neurosurg. Psychia., 31, 207–213 (1968); Hassan, et al., J. Neurol. Neurosurg. Psychia., 43, 1132–1136 (1980); Knutsson, et al., Scand. J. Rehabil. Med., 12, 93–106 (1980); Knutsson, Triangle, 21, 13–20 (1982); Knutsson, et al., J. Neurol. Sci., 53 187–204 (1982); and Kugelbert, Electroenceph. Clin Neurophysiol., Suppl. 22, 103–111 (1962).

The only use for human patients described in the literature for the avermectins, and invermectin in particular, is for treating nematode parasites, particularly onchocerciasis (river blindness) utilizing dosages of up to 150 micrograms per kilogram of body weight. No side effects of significance were reported and no teratogenic activity was found, Pacque, et al., Lancet, 335, 1377–1380 (1990) and Pacque, et al., Lancet, 336, 1486–1489 (1990).

Many members of the avermectin class, in particular invermectin, are potent and highly selective parasiticides which are lethal for invertebrates from a variety of phyla, ranging from insects to nematode worms. Much work has been done to determine the mechanism of action and the safety for use in mammals. Many investigators conclude that ivermectin and avermectin B achieve their results in invertebrates by indirectly potentiating or mimicking the action of the neurotransmitter GABA. See Campbell, et al., Science, 221, 823–828, (1983); Campbell, et al., J. Vet. Pharmacol. Therap., 7, 1–16, (1984); Terada, et al., Exp. Parasitol., 57, 149–157, (1984); Bennett, JAVMA, 189, 100–104, (1986); Chalmers, et al., Eur. J. Pharmacol. 129, 371–374, (1986). Some investigators find other explanations and cast doubt on the accuracy of the GABA agonist theory. See Martin, et al., Br. J. Pharmacol. 98, 747–756, (1989). The parasites are believed to be killed as a consequence of centrally- or peripherally-mediated muscular paralysis. In the families of invertebrates affected, excessive GABA-ergic activity inhibits the process of neuromuscular transmission, see Bennett, supra.

Studies and experiments, attempting to determine if ivermectin exhibits GABA agonistic properties, have shown that ivermectin exhibits such properties in mammalian nervous tissues in vitro, at concentrations ranging from $10^{-7}$M to $10^{-5}$M, with levels of $10^{-6}$M or higher generally being required to produce a 50% change in the parameters studied, Sigel, et al., (1987) supra; Soderlund, et al., (1987) supra; Kirkness, et al., (1988) supra; and Robertson, (1989) supra.

It was found by investigators that intravenous administration of 0.3 mg/kg in rats resulted in very small amounts of ivermectin entering the central nervous system. See Campbell, et al., (1983) supra; Campbell et al., (1984) supra, and Bennett, (1986) supra. Utilizing high doses in dogs and swine resulted in signs suggestive of activity at the level of the central nervous system. See Campbell et al., (1984) supra. However, in the investigations in vitro, the activity of ivermectin does not conclusively demonstrate that it acts as a GABA agonist. The results indicate it has a relatively slow onset of action, loses its activity within minutes of administration, and at times acts as a blocker rather than an activator of GABA-sensitive chloride channels, Sigel, et al., (1987) supra; and Robertson, (1989) supra; In mouse brain preparations, ivermectin may actually inhibit the channel-opening actions of GABA as noted by Soderlund, et al., (1987) supra. In guinea pig brain preparations, investigators found that many actions of ivermectin resemble those of the GABA antagonist picotoxin, Kirkness, et al., Turner (1988) supra.

In investigations to determine the effects of doses large enough to affect the central nervous system of mammals, the clinical signs produced indicated that the central nervous system was profoundly depressed, as evidenced by listlessness and ataxia, followed by loss of upright posture and death, Campbell et al., (1984) supra and Soderlund et al., (1987) supra, citing the unpublished paper of Bloomquist, et al.

There is nothing in the aforesaid publications which shows, speculates or predicts the effects of avermectins in general or ivermectin specifically on humans, i.e. on cardiovascular, gastrointestinal, parasympathetic or sympathetic systems, immune systems, on disease states or dysregulations of the nervous system, or on personality, mood, behavior, memory, attention span or cognitive status. Other GABA agonists known to be active in humans, such as the benzodiazepine tranquilizers, baclofen muscle relaxants and anti-convulsants such as valproic acid and gabapentin, are active to some extent in treating anxiety, as minor anesthesia agents, in treating spasticity, and for seizure control. They also have strong potential to cause cognitive changes, lethargy, somnolence, depression, psychotic behavior, respiratory depression, coma and death, particularly when taken in overdoses or for long periods of time. There is therefore a need for an active agent with GABA agonist properties that possesses all the beneficial effects of the putative GABA agonists, without the potential for toxicity of the other known members of this pharmacological class.

SUMMARY OF THE INVENTION

We have discovered that, surprisingly, the avermectins, when administered to humans in single or multiple doses of up to 1.6 mg/kg of body weight, have the pharmaceutical activities in humans which are generally considered to be due to GABA agonist properties, as well as other activities which may or may not be traceable to GABA agonist properties in humans, and yet are very safe with little or no adverse side effects.

The preferred avermectin for use in this invention is ivermectin, which displays superior effects compared to other so-called GABA agonists when administered in effective amounts as an agent to treat diseases caused by dysregulation or dysfunction of various portions of the nervous system. Thus, this invention is a method for prevention, treatment and control of disease states in humans caused by nervous system dysregulation and dysfunction, which comprises administering to a patient in need of such treatment an effective amount of an avermectin compound. The amount of the avermectin compound administered to be effective is preferably from 0.1 to 1.6 mg/kg of body weight, at intervals of from 3 days to 4 months. The methods of administration are preferably rectal or subcutaneous. The avermectin compound preferred for use in this invention is ivermectin. The methods of prevention, treatment and control for which the active compounds are effective according to this invention are seizure control, diminution of dystonic movements and tremors, significantly decreasing spasticity of both brain and spinal cord origin, e.g. closed head injuries, cerebral palsy, strokes, and spinal cord injuries. In addition, the compounds are effective to increase tonic activity of the parasympathetic nervous system in the bladder and the bowel, to decrease activity of the sympathetic nervous system at cutaneous and cardiovascular levels, to ameliorate depression, to improve mood, to regularize the sleep-wake cycle, to decrease addictive behavior, and to markedly increase the attention span and to improve the behavior of mentally deficient children and adults.

The avermectins are also effective in the re-establishment of normal and appropriate body homeostatic mechanisms. Thus, the compounds are also active in the treatment or palliation of malignancies, or in the alteration of the sensitivity of malignant cells to exogenous chemotherapeutic agents. For the former reason, i.e. re-establishment of normal and appropriate body homeostatic mechanisms, the avermectins are also active in the treatment of rheumatoid arthritis, osteoarthritis, systemic lupus erythematosus, spondylarthropathies, Crohn's disease, ulcerative colitis and connective tissue disorders in general.

DETAILED DESCRIPTION

This invention is based on the discovery that avermectin compounds, including synthetic derivatives thereof, surprisingly have properties which enable them to be used to treat a large number of disease states in humans which are caused, directly or indirectly, by dysregulation and/or dysfunction of various portions of the nervous system.

This invention provides a method of administering an avermectin compound, preferably ivermectin, to patients in need of such administering for preventing, treating and controlling (1) seizure disorders, i.e. epilepsy, (2) diseases associated with damage to or dysfunction of the extrapyramidal system resulting in dystonia and/or tremors, e.g. movement disorders such as Huntington's chorea, familial tremors, muscular dystonia and spastic retrocollis, and congenital degeneration of the basal ganglia, (3) diseases associated with degenerative states such as multi-infarct dementia or Binswanger's dementia, amyotrophic lateral sclerosis, myotonic dystrophy, congenital (hereditary) muscular dystrophies, e.g. Duchenne's and Becker's, motor neuron diseases, spinal muscular atrophy, and Parkinson's disease, (4) diseases caused by acquired lesions of the central nervous system associated with spasticity, e.g. closed head injury, multiple sclerosis, cerebrovascular accidents, cerebral palsy, and meningoencephalitis, (5) spinal cord injury and concomitant spasticity, (6) diseases associated with dopaminergic dysregulation, e.g. schizophrenia and other neuropsychiatric disorders in which excessive dopaminergic activity may play a role, such as manic depressive illness, major affective disorders, behavior disorders and borderline personality states, (7) diseases associated with cortical or subcortical dysregulation of GABA, glutamate, or dopamine, e.g. lesions of peripheral nerves, depression, snoring, sleep apnea, dysregulation of the sleep-wake cycle, seizure disorders, comatose states, causalgia, reflex sympathetic dystrophy, acute or chronic pain associated with the peripheral nervous system, habituation to or dependency on addictive substances, and acute ischemic episodes of varying etiologies such as traumatic closed head injury, subarachnoid hemorrhage, anoxic encephalopathy, infectious or metabolic encephalopathy, and hemorrhagic or embolic/athersclerotic cerebrovascular accidents, (8) dysregulation of the sympathetic and parasympathetic nervous systems, e.g. constipation, hypertension, congestive heart failure, reflex sympathetic dystrophy, causalgia, autonomic hyperreflexia, diabetic neuropathy, renal failure and asthma, (9) cardiovascular disorders caused by excessive activity of the sympathetic nervous system such as angina, hypertension, atherosclerosis, congestive heart failure, and arrhythmias, (10) disorders of behavior, personality, affect, and cognition, e.g. patients in need of cognitive/learning/memory enhancement, depressive states, addictive behavior, mental retardation, sociopathic and psychopathic personality disorders, (11) malignant states, e.g. indirectly by altering the activity of the nervous system or directly by changing the sensitivity of malignant cells to exogenous chemotherapeutic agents and (12) autoimmune disorders in which the nervous system plays a role, such as rheumatoid arthritis, osteoarthritis, systemic lupus erythematosus, spondyloarthropathies, Crohn's disease, ulcerative colitis and general connective-tissue disorders.

The preferred avermectin compound is ivermectin; however, others of the avermectin family of compounds have the same spectrum of activity, even though all the compounds are not equally potent. For example, ivermectin, when administered at dosages from 0.1 to 1.6 mg/kg at intervals of from 3 days to 4 months, causes no significant side effects. Depending on the disease treated, its effects after single-dose administration may last from about three days to about three months. The dosage regimen and strength are determined by the attending clinician's judgment, based on the condition and age of the patient and on the severity and etiology of the disease, as well as on the response to treatment.

The method of administration is preferably rectal, however, subcutaneous, transcutaneous (transdermal), oral, intravenous, intramuscular or intrathecal routes can be used. The dosage forms can be made by conventional means using generally-recognized-as-safe (GRAS) additives, solvents and excipients, taking into account the highly lipophilic nature of the avermectin compounds. Thus the preferred rectal dosage form comprises the active compound dissolved in a suitable solvent such as propylene glycol plus glycerol formal. This same formulation can be used for subcutaneous injections. It is the same formulation used for veterinary purposes under the trademark IVOMEC. The oral dosage can be capsules, tablets, dragees, syrups, and the like. The capsules, tablets and dragees, and other solid oral dosage forms, comprise the active ingredient admixed with a pharmaceutically acceptable carrier vehicle such as starch, talc, magnesium stearate, or dicalcium phosphate. The transdermal dosage form can be a conventional patch generally used to deliver lipophilic drugs.

In using the active compounds of the avermectin family, mixtures of the compounds may be used; this is particularly true when using fermentation products of the C-076 producing microorganisms because the isolated components usually contain a major amount of one component and another amount of a minor component. It is not practical to separate the components, and the biological activity of the major component is negligibly affected. Also, when the fermentation products comprising the two components are derivatized chemically, the components are not separated in either the starting materials or the final product. Thus, the preferred ivermectin compound is normally used as the mixture of at least 80% 22, 23-dihydroavermectin $B_{1a}$ and at most 20% 22, 23-dihydroavermectin $B_{1b}$.

The following examples which illustrate the invention are not intended to limit the invention.

EXAMPLE 1

Ivermectin Injectable Solution

A sterile solution suitable for rectal or subcutaneous administration is prepared using the following formulation to provide a concentration of 10 mg/mL.

| Ingredients | | Amount |
| --- | --- | --- |
| Ivermectin | | 1.0% w/v |
| Glycerol Formal | | 40.0% v/v |
| Propylene Glycol | q.s. | 100.00% v/v |

Dissolve the ivermectin in either the glycerol formal, the propylene glycol or a mixture of the solvents. When the dissolution is complete, adjust the volume to the final desired volume. Sterilize the final solution by membrane filtration and package it aseptically, providing 10 mg of ivermectin per mL of solution.

EXAMPLE 2

Ivermectin Injectable Solution

A sterile solution suitable for rectal or subcutaneous administration is prepared using the following formulation to provide a concentration of 10 mg/mL.

| Ingredients | | Amount |
| --- | --- | --- |
| Ivermectin | | 1.0% w/v |
| Water for Injection | | 10.0% v/v |
| Propylene Glycol | q.s. | 100.00% v/v |

Dissolve the ivermectin in a part of the propylene glycol. Add the water for injection so the precipitation of ivermectin is avoided and adjust the volume with the remaining propylene glycol to the desired final concentration. Sterilize the solution by membrane filtration and package it aseptically.

EXAMPLE 3

Treatment of Seizure Disorders

Eleven patients ages 7 to 79 years were treated with the ivermectin composition prepared in Example 1. The doses ranged from 0.2 mg/kg to 1.3 mg/kg. The methods of administration were either by subcutaneous injection or rectal administration. The ivermectin was administered at intervals of from 3 days to 7 days. Patients Nos. 1–10 were afflicted with epilepsy, manifesting as either absence, focal, or generalized (tonic-clonic) or gran mal seizures. Five patients had concomitant mental retardation and five were of normal intellectual status. One patient, No. 11, had Alzheimer's disease of approximately 4 years' duration, with essentially complete loss of short-term memory. She had evolved to the stage of mild-moderate paranoid ideation and occasional aggressive, combative conduct prior to ivermectin administration.

The following table shows the results.

TABLE 1

| | | Treatment of Normal or Mentally Deficient Patients with or without Seizure Disorders | | | |
| --- | --- | --- | --- | --- | --- |
| Patient No | Type of Seizure | Dosage Amount (mg/kg) | Dosage Frequency | Mode of Administration | Results Observed |
| 1.* | generalized (nocturnal) | 0.2–0.4 | q 5–6 days | subcutaneous or rectal | seizures controlled**, no spasticity, increased attention span, increased responsiveness and emotions |
| 2.* | gran mal | 0.4–0.6 | q 6–7 days | subcutaneous or rectal | seizures controlled**, not aggressive and combative, sleeps |

TABLE 1-continued
Treatment of Normal or Mentally Deficient Patients with or without Seizure Disorders

| Patient No | Type of Seizure | Dosage Amount (mg/kg) | Dosage Frequency | Mode of Administration | Results Observed |
|---|---|---|---|---|---|
| 3.* | none (spastic quadriparesis) | 0.6 | q 5–6 days | subcutaneous or rectal | well, happy, shows emotions much less spasms, happy, non-combative, sleeps well, more interest in surroundings and initiation, improved mobility |
| 4.* | gran mal and absence (very frequent) | 0.7–1.3 | q 5–6 days | subcutaneous or rectal | seizures controlled** better sleep, less agitated, increased attention span |
| 5.* | focal (Jacksonian) (continuous) | 0.4–0.7 | q 3 days | subcutaneous or rectal | seizures controlled sleeps well, now speaks |
| 6. | generalized | 0.2 | weekly | subcutaneous | seizures controlled**, sleeps well, less depression, increased emotional expression |
| 7. | generalized and absence | 0.2–0.3 | weekly | subcutaneous | seizures controlled**, less depression, sleeps well, better mood, stopped snoring |
| 8. | generalized and absence | 0.2–0.4 | weekly | subcutaneous | seizures controlled**, sleeps well, less depressed, increased emotional expression, stopped snoring |
| 9. | generalized and focal (Jacksonian) | 0.2–0.4 | weekly | subcutaneous | seizures controlled**, less depressed, better mood, better stress tolerance |
| 10. | generalized | 0.2–0.3 | weekly | subcutaneous | seizures controlled**, sleeps well, less depressed, no abusive and violent behavior |
| 11. | none (Alzheimer's disease) | 0.2 | weekly | subcutaneous | marked improvement of behavior |

*Mentally retarded
**Decreased or no dose of other anti-epileptic drugs needed after ivermectin As can be seen from the results in Table 1, a considerable degree of seizure control was obtained in all epileptic patients. Administration two times a week was required in some cases. The intellectually normal patients reported improved sleep-wake cycles, resolution of constipation, less angry behavior, less depression, and a markedly better mood. Two patients with partial sleep apnea (Nos. 7 and 8) have stopped snoring at night. The most striking changes have occurred in the patients with seizures and concomitant mental retardation. Aggressive, violent behavior has virtually ceased, and the patients are much more attentive to and affectionate toward the caretaker. Where there previously was apathy and disinterest in the environment, there is now a marked interest in the surroundings and the patients now appear to be capable of pleasure. They have also begun to utter sounds and to attempt to ambulate and to assist in self-feeding and dressing. Severe constipation has resolved, and bladder control is much improved. During the day, the patients signaled the need to urinate and at night bedwetting either stopped or diminished. The patient with Alzheimer's disease has shown marked improvement in her conduct, although memory and orientation remain impaired.

EXAMPLE 4
Treatment of Movement Disorders

Three patients with Huntington's chorea, two patients with generalized (familial) tremor, one patient with muscular dystonia and spastic retrocollis, and two patients with congenital degeneration of the basal ganglia, one patient with dystonia musculorum deformans, and one patient with Parkinson's disease were treated with the ivermectin composition prepared in Example 1. The doses ranged from 0.2 mg/kg to 1.0 mg/kg. The methods of administration were either by subcutaneous injection or rectal administration. The ivermectin was administered at intervals of from 7 days to 4 months.

The following table shows the results.

TABLE 2
Treatment of Movement Disorders

| Patient No. | Disease | Dose Amount (mg/kg) | Dose Frequency | Route of Administration | Results Observed |
|---|---|---|---|---|---|
| 1. | Huntington's chorea | 0.4 | weekly and q month | subcutaneous or rectal | much less intense dystonia, sleeps well, less depressed, better mood, more emotionally |

TABLE 2-continued

Treatment of Movement Disorders

| Patient No. | Disease | Dose Amount (mg/kg) | Dose Frequency | Route of Administration | Results Observed |
|---|---|---|---|---|---|
| 2. | Huntington's chorea | 0.3–0.8 | weekly and q 1–2 weeks | subcutaneous or rectal | responsive 40–50% decrease in dystonia, less depressed, sleeps well, better mood, more emotionally responsive |
| 3. | Huntington's chorea | 0.3–0.6 | weekly and q month | subcutaneous or rectal | much less intense dystonia, less depressed, stopped smoking and drinking, no abusive behavior |
| 4. | generalized tremor (familial) | 0.3–0.4 | weekly and q 2 months | subcutaneous | 90% decrease in tremor sleeps well, speech improved |
| 5. | generalized tremor familial) (with dystonia) | 0.2–0.4 | weekly and q 2 months | subcutaneous | 90% decrease in tremor no dystonia, sleeps well, better mood, not agressive and angry |
| 6. | spastic retrocollis (with dystonia) | 0.2 | q 4 months | subcutaneous | retrocollis and dystonia markedly decreased, sleeps well, better mood |
| 7 | dystonia musculorum deformans | 0.2–1.0 | weekly | subcutaneous or rectal | less dystonia, markedly better body posture |
| 8. | basal ganglia degeneration (familial) | 0.4–0.6 | q 5–10 days | subcutaneous or rectal | 80% decrease in dystonia and spasticity, speech improved, walking improved |
| 9. | basal ganglia degeneration (familial) | 0.4 | weekly | subcutaneous or rectal | much less dystonia and spasticity, speech improved, swallowing better |
| 10. | Parkinson's disease | 0.3 | weekly | subcutaneous or rectal | 100% decrease in rigidity, variable decrease in tremor |

As can be seen from the data in the table, the two patients with generalized (familial) tremor have experienced an estimated 90% reduction in the tremor. In addition, their sleep-wake cycles and frequency of bowel movements have improved, their associated dystonic movements have disappeared, their mood and enjoyment of life is far better, and they are much less depressed. In one of the two patients (patient No. 5), blood pressure after drug administration has remained well controlled despite discontinuation of her usual anti-hypertensive medication. Before drug administration, another patient (patient No. 4) suffered from moderately severe congestive heart failure with 2-pillow orthopnea and frequent paroxysmal nocturnal dyspnea. These symptoms disappeared after the first dose of drug and have not returned.

The data show that the patient with spastic retrocollis is estimated to have 70%-90% less intense and frequent retrocollis spasms. He also reports no pain, less constipation, a regularized sleep-wake cycle, a better mood, and less depression.

The data also show that the three patients with Huntington's chorea have experienced a marked diminution, estimated at 50-80%, of their dystonic movements. In addition, they are no longer irritable, withdrawn and depressed, enjoy life more, sleep better, and report no more constipation. One patient, (patient No. 3) who was frankly abusive to his family and a heavy smoker and drinker, reports that his work performance is better and that he no longer has a desire to smoke or drink. His family reported that his angry mood and abusive behavior have ceased.

As the data show, the two patients with congenital degeneration of the basal ganglia noted an estimated 80% decrease in both spasticity and dystonic movements. They also are no longer constipated, sleep well, and are no longer depressed. Their severe spastic dysarthria has improved, approximately 50% for patient No. 10 and approximately 80% in the case of patient No. 9.

EXAMPLE 5

Treatment of Patients with Acquired Lesions of the Central Nervous System Associated with Spasticity Four patients in this group were treated with the ivermectin composition prepared in Example 1. The doses ranged from 0.1 mg/kg to 0.8 mg/kg. The methods of administration were by subcutaneous injection. The ivermectin was administered at weekly intervals. The following table shows the results.

TABLE 3

Treatment of Patients with Spasticity from Nervous-System Damage

| Patient No. | Disease | Dosage Amount mg/kg | Dosage Frequency | Route of Administration | Results Observed |
|---|---|---|---|---|---|
| 1. | left cerebrovascular accident (ischemic) | 0.3 | weekly | subcutaneous | decreased spasticity, gait better, marked |

TABLE 3-continued

Treatment of Patients with Spasticity from Nervous-System Damage

| Patient No. | Disease | Dosage Amount mg/kg | Dosage Frequency | Route of Administration | Results Observed |
|---|---|---|---|---|---|
| 2. | meningo-encephalitis | 0.2–0.8 | weekly | subcutaneous | improvement in speech fluency markedly decreased spasticity, gait better |
| 3. | left cerebro-vascular accident (hemorrhagic) | 0.1–0.6 | weekly | subcutaneous | less spasticity, gait better |
| 4. | left cerebro-vascular accident (schemic) | 0.1–0.3 | weekly | subcutaneous | less spasticity, gait better improvement in speech fluency |

As is apparent from the data in Table 3, the spasticity of each of the patients decreased, and all had increased fluidity of movement and improved gait. The most striking change in the aphasic patients was more fluent and less dysarthic speech.

EXAMPLE 6

Treatment of Spasticity Caused by Spinal Cord Injury

Thirteen patients with spinal cord injury and concomitant spasticity were treated with the ivermectin composition prepared in Example 1. The doses, which were administered in an ascending-dose fashion, ranged from 0.2 mg/kg to 1.6 mg/kg. The methods of administration were either by subcutaneous injection or rectal administration. The etiologies included trauma from gunshot wound (patients Nos. 2, 4, 10, 11, 12, and 13), blunt trauma (patients Nos. 1, 8, and 9), penetrating instrument wound (patient No. 3), arachnoiditis (patient No. 5), tropical spastic paraparesis (patient No. 6), and cervical myelopathy (patient No. 7). The ivermectin was administered at intervals of from 7 days to 3 months. The following table shows the results.

TABLE 4

Treatment of Spasticity Caused by Spinal Cord Injury

| Patient No. | Nature of Injury | Dosage Amount mg/kg | Dosage Frequency | Route of Administration | Results Observed* |
|---|---|---|---|---|---|
| 1. | C8-T1 contusion; Frankel Class A | 0.2–1.2 | biweeky and q 2–3 months | subcutaneous | 100% decreased spasms, tone normal stands with support, moves feet, sensation unchanged |
| 2. | T4 gunshot wound; Frankel Class A | 0.2–1.6 | biweekly and q 2 months | subcutaneous | 80% decreased spasms, tone normal, stands and crawls, sensation to L4 level |
| 3. | C5 knife wound; Frankel Class C | 0.2–1.2 | biweekly and q 3 months | subcutaneous | 100% decreased spasms, tone normal, better gait, better sensation |
| 4. | C5 gunshot wound; Frankel Class C | 0.2–0.8 | biweekly and q 3 months | subcutaneous | 80-100% decreased spasms, tone normal, stands, sensation to L5-S1 level |
| 5. | lumbar arachnoiditis; Frankel Class D | 0.2–1.2 | biweekly and q week | subcutaneous | 80-100% decreased spasms, tone normal, walks with walker, better sensation |
| 6. | tropical spastic paraparesis; Frankel Class D | 0.2–1.0 | biweekly | subcutaneous | 100% decreased spasms, tone still high, better walking, sensation unchanged (normal) |
| 7. | C5 cervical myelopathy; Frankel Class C | 0.2–0.4 | biweeky and q week | subcutaneous | 80-100% decreased spasms, tone normal walks with support, sensation unchanged (normal) |
| 8. | T6 fracture-dislocation; Frankel Class A | 0.4–0.6 | biweekly and q week | subcutaneous | 80% decreased spasms, tone normal stands, sensation unchanged |
| 9. | C5-6 fracture-dislocation; Frankel Class B | 0.45 | weekly | subcutaneous | 80% decreased spasms, tone normal no data on motor and sensory function |
| 10. | T5 gunshot wound; | 0.2–1.2 | biweekly and | subcutaneous | 80-100% decreased |

TABLE 4-continued

Treatment of Spasticity Caused by Spinal Cord Injury

| Patient No. | Nature of Injury | Dosage Amount mg/kg | Dosage Frequency | Route of Administration | Results Observed* |
|---|---|---|---|---|---|
| | Frankel Class A | | q week | or rectal | spasms, tone normal, better trunk control, sensation to L1 level |
| 11. | C8 gunshot wound; Frankel Class B | 0.4–0.8 | weekly | subcutaneous | no data on motor and sensory function |
| 12. | T1 gunshot wound; Frankel Class B | 0.3–0.6 | weekly | subcutaneous | decreased spasms, improved sensation |
| 13. | C2 gunshot wound; Frankel Class B | 0.2 | single dose | subcutaneous | no changes noted |

*Results only on spasms, tone, and motor plus sensory function. See text for other observations.

The data show that as a result of the treatment, at least 10 of the 13 patients showed a marked (80–100%) decrease in spasms. Concomitantly, there was a reduction in muscle tone to normal levels.

In addition, in most cases, the anti-spasticity effects were transient, that is, they lasted 24–96 hours or were absent, at doses of 0.2–0.4 mg/kg of body weight. More positive effects became apparent at doses of 0.6–1.6 mg/kg. At the higher dosage range, spasms were essentially completely abolished, and this effect persisted for intervals up to three months after the last dose of ivermectin. There were clear dose- and time-response relationships as the doses increased in all the patients who received successive doses, with progressively greater decreases in the severity of the spasms and longer periods of spasm diminution or absence after the administration of each dose. Other noteworthy changes included improved mood and emotional status, less depression, improved sexual function, better bladder and bowel action and regulation, moderate to marked improvement in the extent of cutaneous sensation below the level of the lesion, i.e. from T4 to L4, or from C5 to S1, and a decrease in excessive sympathetic nervous-system activity, i.e., less profuse sweating above the level of the lesion.

Using the composition of Example 1 and the dosage regimen of Example 6, the avermectins are expected to interact with G proteins (G proteins bind to guanosine nucleotides), which are utilized in many organs of the body, including the nervous system, to transmit signals to the interior of cells following the binding of molecules to receptors on the cell surface. In addition to being involved with neurotransmitter release and action, G proteins are also present in malignant cells, where they appear to play a role in the creation and maintenance of the malignant state, see Marx, Research News, 1317, (Mar. 15, 1991). The G proteins may also be associated with the development of resistance to chemotherapeutic agents. See Gisslinger, et al., Lancet, 336, 1078, (1990). By blocking a G protein active site, the avermectins are expected to successfully treat and palliate malignancies, as well as to reduce or eliminate development of resistance to chemotherapeutic agents. It is also expected the avermectins would facilitate the re-establishment of normal and appropriate body homeostatic mechanisms via their actions on the nervous system.

In addition it is expected that the avermectins will, because of their effects on the nervous system, be useful to treat autoimmune diseases in which the nervous system plays a role, e.g. rheumatoid arthritis, osteoarthritis, systemic lupus erythematosus, spondyloarthropathies, Crohn's disease, ulcerative colitis, and other connective-tissue disorders. See Levine, et al., Science, 226, 547–549, (1984), Thompson, et al., Ann. Rheum. Dis. 21, 370–377, (1962), and Bland, et al., Arthritis and Rheum., 11, 72–79, (1968).

We claim:

1. A method for preventing, treating or controlling spasticity diseases of human nervous system dysregulation and/or dysfunction, which comprises administering to a patient in need of such preventing, treating or controlling an effective amount of a compound of the avermectin family.

2. A method of claim 1 wherein the human nervous system dysregulation and/or dysfunction disease which is prevented, treated or controlled is selected from spasticity caused by lesions of the central nervous system and spasticity caused by spinal cord injury.

3. A method of claim 1 wherein the avermectin compound administered is ivermectin.

4. A method of claim 1 wherein the avermectin compound is administered at doses up to 1.6 mg/kg at intervals of from 3 days to 4 months.

5. A method of claim 2 wherein the spasticity prevented, treated, or controlled is caused by head injury, encephalopathy, multiple sclerosis, cerebrovascular accident, or spinal cord damage.

6. A method of claim 1 wherein the method of administration is rectal.

7. A method of claim 1 wherein the method of administration is subcutaneous injection.

8. A method of claim 1 wherein the method of administration is oral.

9. A method of claim 1 wherein the method of administration is transdermal.

* * * * *